United States Patent [19]
Bartlett et al.

[11] Patent Number: 5,391,203
[45] Date of Patent: Feb. 21, 1995

[54] METHOD OF DRAINING AND FILLING SOFT TISSUE IMPLANT

[75] Inventors: Scott P. Bartlett, 500 W. Moreland Ave., Chestnut Hill, Pa. 19118; Kant Lin, Charlottesville, Va.; Kiyoshi Matsuo, Matsumoto, Japan

[73] Assignees: Scott P. Bartlett, Philadelphia; Linton A. Whitaker, Wynnewood, both of Pa.

[21] Appl. No.: 867,992

[22] Filed: Apr. 13, 1992

[51] Int. Cl.6 .............................................. A61F 2/12
[52] U.S. Cl. ........................................ 623/8; 623/11; 623/12; 606/191
[58] Field of Search .................... 623/1, 8, 11, 12; 604/266; 600/36; 606/191

[56] References Cited

U.S. PATENT DOCUMENTS

| | | |
|---|---|---|
| 4,141,973 | 2/1979 | Balazs . |
| 4,500,676 | 2/1985 | Balazs et al. . |
| 4,624,671 | 11/1986 | Kress ............................ 623/8 |
| 4,731,081 | 3/1988 | Tiffany et al. . |
| 4,795,463 | 1/1989 | Gerow . |
| 4,803,075 | 2/1989 | Wallace et al. . |
| 4,828,561 | 5/1989 | Woodroof ...................... 623/8 |
| 4,880,429 | 11/1989 | Stone . |
| 4,904,260 | 2/1990 | Ray et al. . |
| 4,955,909 | 9/1990 | Ersek et al. . |
| 4,963,150 | 11/1990 | Brauman . |
| 4,995,882 | 2/1991 | Destonet et al. . |
| 5,067,965 | 11/1991 | Ersek et al. . |
| 5,219,360 | 6/1993 | Georgiade ..................... 623/8 |

OTHER PUBLICATIONS

Beisang, et al., Radiolucent Prosthetic Gel, *Plastic and Reconstructive Surgery*, pp. 885–892, May 1991.

Whalen, R. L., Connective tissue response to movement at the prosthesis/tissue interface, *Biocompatible Polymers, Metals & Composites*, M. Szycher, ed., Lancaster, Pa., Technomic Pub. Co., Inc., 1983, pp. 953–974.

Cronin & Gerow, Augmentation Mammaplasty: A New "Natural Feel" Prosthesis, *Transactions of the Third International Congress of Plastic and Reconstructive Surgery*, Amsterdam: Excerpta Medica, pp. 41, 1964.

King, S. R., M.D., Hickerson, W. L., M.D., Proctor, K. L., PhD., "Beneficial actions of exogenous hyaluronic acid on wound healing," *Surgery* vol. 109, No. 1, 76–84 (1991).

*Primary Examiner*—Paul Prebilic
*Attorney, Agent, or Firm*—Woodcock Washburn Kurtz Mackiewicz & Norris

[57] ABSTRACT

This invention provides prostheses for implantation into human soft tissue. One aspect of this invention provides soft tissue prostheses comprising a physiologically compatible containment sac and, contained within said sac, a normal body constituent comprising a glycosaminoglycan, mucopolysaccharide, or any other naturally occurring, highly viscous filling material known to be rapidly resorbed from tissues or known to cause little adverse tissue reaction. Also provided by this invention are methods for recontouring soft tissue at a selected body location and methods for decreasing the risk of adverse physiological reaction to an implant.

8 Claims, 1 Drawing Sheet

METHOD OF DRAINING AND FILLING SOFT TISSUE IMPLANT

FIELD OF THE INVENTION

This invention relates to prostheses for implantation into human soft tissue, especially in the region of the breast.

BACKGROUND OF THE INVENTION

Implantable prostheses have been used to recontour human soft tissue since at least the early 1950's. The most frequently used prostheses are breast prostheses. More than 2 million women have prosthetic breast implants and this number-continues to grow with an additional 200,000 breast prostheses implanted in the United States each year. Beisang, et al., Radiolucent Prosthetic Gel, *Plastic and Recon. Surgery*, 885–892, May 1991. Breast prostheses may be used for cosmetic or reconstructive purposes, for example, following a radical mastectomy or other trauma to the soft tissue of the breast. Notwithstanding the frequency of breast augmentation procedures, there are potentially severe complications associated with the implants used for such procedures.

Capsular contracture around an implant is the principal cause for dissatisfaction among implant recipients. Encapsulation is a natural response of human soft tissue to a foreign material, such as a prosthetic implant. The body perceives the implant as a foreign material which can neither be dissolved nor extruded and, in an effort to isolate the foreign material, the body forms a collagen-capsule around the implant; All implants elicit this foreign body reaction. Under normal healing circumstances, once a capsule is formed, the inflammatory reaction should cease. Persistent irritation may cause the capsule to contract around the soft implant, precipitating the development of thick fibrous scar tissue that makes the breast feel hard and painful to the touch and results in dissatisfaction and even deformity. Whalen, R. L., Connective tissue response to movement at the prosthesis/tissue interface, *Biocompatible Polymers, Metals & Composites*, M. Szycher, ed., Lancaster, Pa. Technomic Pub. Co., Inc., 1983, pp. 953–974.

The most common breast implant, the silicone-filled implant, comprises a hollow shell filled with silicone oil or silicone gel. Cronin & Gerow, Augmentation Mammaplasty: A New "Natural Feel"Prosthesis, *Transactions of the Third International Congress of Plastic and Reconstructive Surgery*, Amsterdam: Excerpta Medica, pp. 41, 1964. The leakage of silicone oil or silicone gel into the surrounding soft tissue may be caused, for example, by a compromise in the shell integrity, such as is caused by surgery or trauma. But even in the absence of such traumatic event, silicone oil continually migrates through the wall of the implant into surrounding tissue. Some of the complications associated with silicone-filled breast prostheses are related to the body's inability to eliminate the silicone oil. The silicone accumulates and a chronic inflammatory reaction may result. It has also been suggested that leakage of silicone into the surrounding soft tissue may induce auto-immune disorders.

Any of the foregoing may necessitate extensive surgery to remove the implant. But removal is not always a complete treatment. Due to the potential systemic nature of some of the complications, such complications may persist beyond such removal of the offending implant. Beisang, supra.

In addition to the foregoing, because silicone is radiographically dense, silicone-filled breast prostheses may obscure mammographic resolution. This may conceal microcalcifications and soft tissue masses and delay the detection of cancerous masses. This is quite significant when it is considered that one in nine women will eventually experience breast cancer and that cancer will recur in one of three of these women. Beisang, supra. Many of these women will have reconstructive surgery which utilizes prosthetic implants that may delay the detection of recurrence.

Despite the potentially severe complications and interference with mammographic techniques for the detection of masses, silicone-filled implants have gained widespread acceptance. This has prompted research related to improving prosthetic implants.

With respect to breast implants, several inventors have suggested that the foreign body reaction precipitated by prosthetic implants may be controlled by altering the host-prosthesis interface. Accordingly, numerous attempts have been made to change the outer shell in a manner that decreases or minimizes the foreign body reaction. For example, U.S. Pat. No. 4,955,909, in the name of Ersek, et al., discloses an implant having a shell with a textured surface. It is suggested that the textured surface will allow for fibroblast ingrowth into the interstices of the shell and thus prevent micromotion at the host-prosthesis interface thereby decreasing the amount of scar tissue formed.

U.S. Pat. No. 4,963,150, in the name of Brauman, discloses an implant shell comprising a flexible container having an outer plastic covering that is rough textured with numerous pores or interstices. It is suggested that this plastic covering may prevent the contracture of surrounding tissue.

U.S. Pat. No. 4,731,081, in the names of Tiffany, et al., discloses a rupture-resistant prosthesis. The prosthesis is rendered rupture-resistant by injecting a liquid with uniformly dispersed lubricating material into a flexible, creasable shell during manufacture or surgical implantation. The lubricating material may reduce frictional wear along opposed inner surfaces during sliding contact in a creased area in the shell wall after implantation.

Despite prior attempts, a rupture-proof or leak-proof shell has not been developed. In U.S. Pat. No. 4,795,463, Gerow disclosed an implant labeled with radiopaque markers so that roentgenographic imaging may be used to determine whether the shell has ruptured or whether the shell is folded persistently in a particular location increasing the probability that the envelope may rupture along the fold line.

Unfortunately, knowing that the shell has ruptured or is likely to rupture does not necessarily avoid the complications resulting from leakage of the filling material, for example, silicone, into surrounding soft tissue. Some inventors have suggested changing the filling material of the implants to a material less likely to precipitate such a severe adverse reaction if it should leak into soft tissue. One such filling suggested is saline. A great advantage to the saline-filled implants, as compared to the silicone-filled implants, is that the leakage of saline into surrounding soft tissue is not associated with the systemic complications that may result from silicone leakage. In addition, as compared to the silicone-filled implants, the saline-filled implants are relatively radiolucent, i.e., they do not obstruct mammographic resolution to the extent that silicone does and thus are less like to obscure detection of small masses by mammography. Yet despite these advantages, saline-filled implants have not been nearly as popular as silicone-filled implants. One disadvantage to the saline-filled implants, is that they have a 1% spontaneous deflation rate due to the prevalence of fold-flaw fractures and valve leakage. Beisang, supra. However, the lack of popularity of saline-filled implants is more readily attributable to the lack of viscosity. Simply stated, saline lacks the viscosity of silicone, and it is the viscosity which provides a consistency which more closely mimics the consistency of human breast tissue. Implant recipients want the implants to closely mimic the consistency of human soft tissue.

Inventors have searched for a more viscous implant filling material. U.S. Pat. No. 5,067,965 suggests using a radiolucent bio-osmotic gel medium filling comprising a bio-compatible organic polymer in a solution of bio-compatible salt of relatively low Z number wherein said filling is excretable by the body, has an osmolarity of from about 250 milliosmoles to 350 milliosmoles and an x-ray absorption approximately equal to that of breast tissue under standard exposure. One such material suggested by the disclosure in polyvinylpyrollidone. If the implant should rupture, the gel should preferably be removed from the body by irrigation of the tissues. The remaining gel material is removed by the reticuloendothelial system and excreted through the kidneys.

Another alternative, is a breast implant filled with a biocompatible triglyceride such as peanut oil or sunflower seed oil, as disclosed in U.S. Pat. No. 4,995,882 in the name of Destonet, et al. This implant purportedly duplicates the photoelectric interaction of fat which is both a substantial component of human breast tissue and the major producer of subject contrast at low radiation levels as used in mammography. Thus it is better radiographically than silicone-filled implants. However, the filling used in this implant, similar to saline, lacks the viscosity of silicone gel.

In the past, despite the availability of purportedly safer alternatives, silicone-filled implants were the most frequently used implants. Even after the recent FDA moratorium on silicone-filled implants and extensive adverse publicity, the use of such implants persists. There is an urgent need for the development of an implant filled with a viscous material that causes little adverse tissue reaction if it comes in contact with the surrounding soft tissue.

OBJECTS OF THE INVENTION

It is an object of this invention to provide soft tissue prostheses containing a filling comprising a viscous material that, if it should come in contact with the surrounding soft tissue, causes little adverse tissue reaction.

A further object of this invention is to provide soft tissue prostheses containing a viscous filling material that, upon palpation, may closely mimic the consistency of human breast tissue.

A further object of this invention is to provide methods of recontouring a soft tissue body portion comprising implanting into said soft tissue a prosthetic containing a viscous material known to be rapidly resorbed from tissues or known to cause little adverse tissue reaction.

It is a further object of this invention to provide soft tissue prostheses capable of being adapted for implantation into human soft tissue at a selected body location to establish a desired body contour, wherein said prostheses contain a viscous filling material known to be rapidly resorbed from tissues or known to cause little adverse tissue reaction.

It is a further object of this invention to provide methods for diminishing the risk of adverse physiological reaction to a soft tissue implant, for example, a silicone-filled implant.

These and other objects of the present invention will be apparent from a review of the instant specification and attendant claims.

SUMMARY OF THE INVENTION

This invention accomplishes the foregoing objectives by providing soft tissue prostheses, especially, mammary prostheses, that are filled with a material which, if it should come in contact with the surrounding soft tissue, would cause little adverse tissue reaction and, in fact, may actually facilitate healing with decreased scar tissue formation. The implants of this invention further overcome limitations in the prior art because they utilize a highly viscous filling material that, upon palpation, may closely mimic the consistency of human breast tissue. In addition, the implants of this invention are radiographically more desirable than certain other implants.

It is anticipated that prostheses described herein may be used at various selected body locations to establish a desired body contour and, accordingly, may comprise varying dimensions. Filling materials utilized herein may comprise any naturally occurring, highly viscous material, for example, glycosaminoglycans, mucopolysaccharides, or a combination thereof. Such filling materials may be contained within any physiologically compatible containment sac capable of adaptation for implantation into human soft tissue and the dimensions of such containment sacs vary according to location of implantation and result desired. The prostheses may be provided for implantation in a pre-filled form or the filling and sac may be provided separately. When provided separately, the sac may be filled with the filling in the procedure or operating room, prior to implantation.

This invention further provides methods for diminishing the risk of adverse physiological reaction to an implanted prosthesis without surgically removing the implant. In such methods, the undesired filling material may be withdrawn from an implanted containment sac, the containment sac filled with a desired filling material, and the sac drainage or aspiration site sealed.

DETAILED DESCRIPTION OF THE INVENTION

Provided by this invention, are soft tissue prostheses comprising a physiologically compatible containment sac and, contained within said sac, a naturally occurring, high viscosity filling material.

Figure 1:
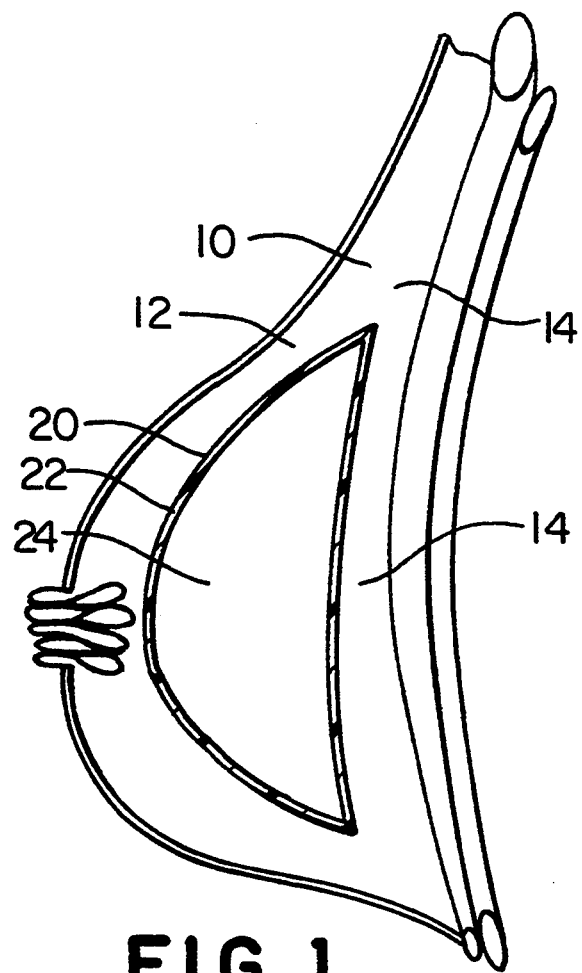
FIG. 1. A cross section visualization of a reconstructed human breast with an implanted prosthesis.

FIG. 1 shows a diagrammatic representation of a soft tissue prosthesis 20 for implantation into the soft tissue 14 of the human breast 10. The prosthesis 20 comprises a physiologically compatible containment sac 22 and, contained within said sac, a naturally occurring, high viscosity filling material 24.

Figure 2:
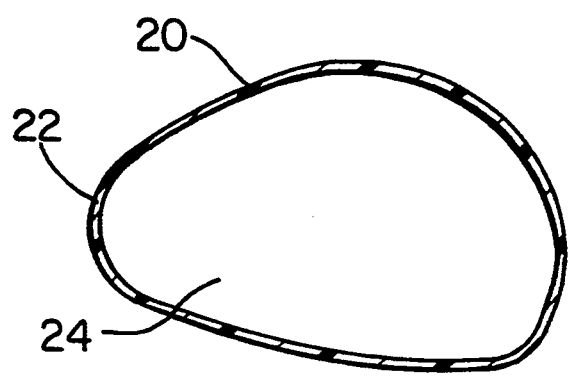
FIG. 2. A soft tissue implant comprising a physiologically compatible containment sac containing a naturally occurring, high viscosity filling material, for example, hyaluronic acid.

FIG. 2 shows a diagrammatic representation of a soft tissue prosthesis 20 comprising a physiologically compatible containment sac 22 and, contained within said sac, a naturally occurring, high viscosity filling material 24.

As used herein, "containment sac" includes any pouch, sac, shell, or other structure capable of substantial containment, having dimensions appropriate to substantially provide the desired augmentation or body contour, and capable of adaption for implantation into human soft tissue, including but not limited to, a silastic shell comprising medical grade silicone.

Naturally occurring, high viscosity filling materials include glycosaminoglycans, mucopolysaccharides, or any other highly viscous normal body constituent known to be rapidly resorbed from soft tissue or known to cause little adverse tissue reaction. Examples of glycosaminoglycans include hyaluronic acid, chondroitin 4-sulfate, chondroitin 6-sulfate, dermatan sulfate, heparin sulfate, and keratan sulfate. Examples of mucopolysaccharides include hyaluronic acid and sodium hyaluronate.

Hyaluronic Acid is a naturally occurring, high viscosity, linear mucopolysaccharide comprised of alternating glucuronic acid and N-acetyl-glucosamine residues that interacts with other proteoglycans to provide stability and elasticity to the extracellular matrix of all tissues. King, S. R., M.D., Hickerson, W. L., M.D., Proctor, K. L., Ph.D., "Beneficial actions of exogenous hyaluronic acid on wound healing," *Surgery* Vol. 109, No. 1, 76-84 (1991). Hyaluronic acid is a clear, viscous fluid, manufactured and commercially available in a purified form for use in ophthalmic vitreous body implants and synovial joint replacements. Purified hyaluronic acid is believed to cause very little tissue reaction once spilled into the soft tissue. In fact, the known actions of hyaluronic acid are consistent with a role in wound healing with minimal fibroblast proliferation and infiltration.

U.S. Pat. No. 4,141,973, issued Feb. 27, 1979, in the name of Balazs, discloses an ultrapure hyaluronic acid fraction and its sodium salt form. Prior to this invention, many high molecular weight purified hyaluronic acid preparations were known, however, these preparations were not suitable substitutes for the vitreous humor and/or synovial fluid because they contained some unidentified impurity which caused inflammation. Balazs identified an ultrapure high molecular weight hyaluronic acid suitable for in vivo use because it did not precipitate inflammatory activity. Balazs further identified three major areas for use of this ultrapure hyaluronic acid: to prevent fibrous tissue formation; to separate tissue surfaces; and for the protection of skin wounds.

Hyaluronic acid has been employed in several subsequent inventions. U.S. Pat. No. 4,500,676, in the name of Balazs, et al., relates to polymeric articles modified with hyaluronic acid to give them improved biocompatibility. Such articles may be used in numerous in vivo applications, including prosthetic devices such as artificial heart valves, vascular grafts, and the like. The hyaluronic acid may be either dispersed throughout the polymeric article, used as a coating on the surface thereof, or both.

U.S. Pat. No. 4,803,075, in the name of Wallace et al., discloses an injectable implant composition for soft tissue augmentation comprising an aqueous suspension of a particulate biomaterial containing a sufficient amount of a biocompatible fluid lubricant, for example, hyaluronic acid, to improve the intrudability of the composition. In this invention, soft tissue augmentation is achieved by injecting the composition into the augmentation site. The invention further provides a method for improving the injectability of implant suspensions of particulate biomaterials, such as collagen, by incorporating a lubricant, such as hyaluronic acid, into the suspension.

U.S. Pat. No. 4,880,429, in the name of Stone, disclosed a structure for implantation into the knee joint which assumes the form and role of a meniscus, and may also promote regrowth of meniscal tissue and provide a scaffold for regenerating tissue. The structure is an array of collagen fibers interspersed and crosslinked with glycosaminoglycan molecules, for example, hyaluronic acid. More specifically, the prosthetic meniscus is composed of a porous dry volume matrix of Type I collagen fibers interspersed with glycosaminoglycan molecules, wherein said matrix has a substantially wedge shape including a wide central region between two narrow distal tip regions, wherein at least a portion of said molecules provide glycosaminoglycan crosslinks between said collagen fibers. The glycosaminoglycan molecules may be uniformly dispersed throughout the prosthesis as individual molecules, or present in differing amounts in different regions of the structure. At least a portion of the molecules are constituents of chemical crosslinks which bridge neighboring collagen fibers.

U.S. Pat. No. 4,904,260, in the names of Ray, et al., discloses a cylindrical prosthetic intervertebral disc having a flexible bladder comprising a semi-permeable membrane enclosing a fluid containing a therapeutic material that is slowly diffusible through the semipermeable membrane, and a layer of strong fibers encompassing the fluid-filled membrane. The fluid enclosed in the bladder preferably is a thixotropic gel having a viscosity and velocity-shear behavior imitating the natural rheology of intradiscal nuclear tissue. The thixotropic gel may be hyaluronic acid.

The prosthetic device disclosed by Ray, et al., is both a structural element and a pharmacologically active device. The pharmacologically active device claimed comprises a flexible bladder which is chemically and biologically inert and which comprises a semi-permeable membrane through which a therapeutic material may slowly diffuse but through which cells will not pass. The structure claimed comprises an elongated cylindrical prosthetic intervertebral disc capsule having a diameter approximating the height of a human disc space and a length approaching the sagittal diameter of the vertebral body.

Heretofore, the use of hyaluronic acid as a filling for soft tissue prostheses has not been suggested. Applicants herein have discovered that this viscous mucopolysaccharide provides an implant with a consistency that, when compared to saline and triglyceride fillings, more closely mimics the consistency of human breast tissue. Further, when compared to silicone, the leakage of hyaluronic acid is not likely to precipitate the number and severity of complications associated with silicone leakage. In fact, if the integrity of the implant shell should become compromised, the hyaluronic acid which leaks into surrounding soft tissue may actually facilitate healing in the area with decreased scar tissue formation and thus irrigation of the soft tissue would not be necessary. In addition, the use of a hyaluronic acid filling provides an implant that is relatively radiolucent when compared to silicone-filled implants. This invention overcomes limitations in the prior art and satisfies long felt needs in the areas of augmentation mammoplasty and soft tissue implantation.

Those skilled in the art will recognize that, whenever available, the filling material contained within said containment sac should be in a form known to be physiologically compatible, i.e., known to cause little inflammatory reaction. For example, if the filling comprises hyaluronic acid, the ultrapure form of hyaluronic disclosed by Balazs in U.S. Pat. No. 4,141,973, cited herein and incorporated by reference, would be preferred.

Said prostheses may be implanted to establish a desired body contour in the soft tissue of the human breast or at any other selected body location. Methods for implantation of a prosthetic device into human soft tissue, including procedures for implanting breast prostheses, are well known to those of ordinary skill in the art of augmentation surgery.

Provided herein are prostheses for implantation into human soft tissue comprising a physiologically compatible containment sac and, contained within said sac, a glycosaminoglycan. One embodiment provides soft tissue prostheses comprising a physiologically compatible silastic sac of medical grade silicone and, contained within said sac, hyaluronic acid.

Further provided by this invention are prostheses comprising a physiologically compatible containment sac and, contained within said sac, a mucopolysaccharide, said prosthesis being adapted for implantation into human soft tissue at a selected body location to establish a desired body contour. In one embodiment, said prostheses comprise a containment sac of medical grade silicone, and contained within said sac, hyaluronic acid.

Further provided are prosthetic soft tissue implants comprising a physiologically compatible containment sac and, contained within said sac, a normal body constituent known to be rapidly resorbed from tissues or known to cause little adverse tissue reaction. In one embodiment, said prosthetic soft tissue implants comprise a silastic sac of medical grade silicone and, contained within said sac, hyaluronic acid.

The prostheses of this invention may be provided for implantation in a pre-filled form or the filling and sac may be provided separately. When provided separately, the sac may be filled with said filling in the procedure or operating room, just prior to implantation. In one embodiment, a physiologically compatible containment sac of medical grade silicone and hyaluronic acid filling are provided separately, and said sac is filled with said hyaluronic acid in the procedure or operating room, prior to implantation.

Methods of recontouring human soft tissue using soft tissue prostheses are also provided by this invention. In one embodiment, said method comprises implanting into said soft tissue a hyaluronic acid-filled prosthetic implant. The hyaluronic acid is contained within a physiologically compatible sac, for example, a silastic containment sac of medical grade silicone.

Methods of diminishing the risk of adverse physiological reaction to a mammalian soft tissue implants are also provided by this invention. In one embodiment, said method comprises the steps of withdrawing the filling material contained within an implanted prosthesis by drainage or aspiration, irrigating said containment sac with a composition capable of removing any residual filling material, refilling said containment sac with a naturally occurring, high viscosity filling material that is less likely to precipitate an inflammatory reaction if it should leak into the surrounding soft tissue, and sealing the sac drainage or aspiration site.

Methods for draining or aspirating matter contained within an implanted prosthesis and irrigating the containment sac are well known to those of ordinary skill in the art. Methods for introducing matter into an implanted prosthesis and sealing the containment sac are also well known to those of ordinary skill in the art.

In one embodiment, the filling material is withdrawn from a silicone-filled breast implant and said containment sac is refilled with hyaluronic acid. In other embodiments, said filling material withdrawn may comprise saline, collagen gel, a triglyceride of polyvinylpyrollidone, said refilling material may comprise any naturally occurring high viscosity mucopolysaccharide or glycosaminoglycan. Said implant may be at a location other than the breast.

Variations and modifications of the aforementioned can, of course, be made without departing from the spirit and scope of the invention as disclosed herein, and those skilled in the art will recognize multiple utilizations of the present invention that are within the scope of this disclosure.

EXAMPLES

Example 1

To determine the feasibility of a hyaluronic acid filled prosthetic implant as a substitute to the conventional silicone gel and saline filled implants, one of each of three types of custom made breast prostheses consisting of a silastic shell filled with 6 cc of either silicone gel, saline or hyaluronic acid, measuring 21 mm×10 mm was implanted into the subcutaneous tissue on the backs of rabbits using a model known in the art and described in Plastic and Recon. *Surgery* 57:637 (1976).

Twenty-four adult rabbits were broken down into three groups of eight animals, to be studies for 3, 6, and 12 months prior to sacrifice. At sacrifice, the implant and surrounding soft tissue was removed en bloc. Soft tissue was examined histologically using standard H & E preparations.

Results indicated there is less soft tissue capsule formation around hyaluronic acid filled implants and a lesser inflammatory response histologically, as compared to the silicone-filled or saline-filled implants.

Example 2

Eight adult rabbits were injected with 6 cc of hyaluronic acid directly into the subcutaneous tissue, simulating an implant rupture. The animals were sacrificed and tissue harvested at 1, 3, 7 and 10 days, at which time the soft tissue was examined histologically for evidence of an inflammatory reaction to the free hyaluronic acid. Alcian Blue stain was used to test for the presence of residual hyaluronic acid.

Results indicated an early infiltrative response to the injected material which was completely normalized by 10 days.

Example 3

Custom made 50 cc prosthetic implants filled with either silicone, peanut oil, saline or hyaluronic acid, were studied for their radiographic characteristics in accordance with a method known to those of ordinary skill in the art and described in *Plastic and Recon. Surgery* 84:772 (1989). Radiographs were taken through silicone filled and hyaluronic filled implants and compared for radiodensity and degree of artifact resolution loss.

Hyaluronic acid filed implants were equivalent to saline implants, being the most radiolucent and allowing for accurate radiographic resolution of materials through the implants.

We claim:

1. A method for diminishing the risk of adverse physiological reaction to a mammalian soft tissue implant of the type having a containment sac containing a filling, comprising the steps of draining or aspirating said filling from said sac, irrigating said sac, introducing a mucopolysaccharide filling into said sac, and sealing the sac drainage or aspiration site.

2. A method of claim 1 wherein said mucopolysaccharide is hyaluronic acid or sodium hyaluronate.

3. A method of claim 1 wherein said mucopolysaccharide is hyaluronic acid.

4. A method of claim 1 wherein said mammalian soft tissue implant is implanted in human breast tissue.

5. A method of claim 1 wherein said filling drained or aspirated from said containment sac is silicone.

6. A method of claim 1 wherein said filling drained or aspirated from said containment sac is a saline solution.

7. A method of claim 1 wherein said filling drained or aspirated from said containment sac is a collagen gel, a purified gel of poly-alpha amino acid homopolymers or random copolymers having a molecular weight of from 5,000 to 40,000.

8. A method of claim 1 wherein said filling drained or aspirated from said containment sac is a triglyceride.

* * * * *